US009968801B2

(12) United States Patent
Sumanaweera et al.

(10) Patent No.: US 9,968,801 B2
(45) Date of Patent: May 15, 2018

(54) RADIATION TREATMENT PLANNING AND DELIVERY FOR MOVING TARGETS IN THE HEART

(71) Applicant: CyberHeart, Inc., Mountain View, CA (US)

(72) Inventors: Thilaka Sumanaweera, Los Altos, CA (US); Patrick Maguire, Portola Valley, CA (US); Edward Gardner, San Jose, CA (US)

(73) Assignee: CyberHeart, Inc., Mountain View, CA (US)

( * ) Notice: Subject to any disclaimer, the term of this patent is extended or adjusted under 35 U.S.C. 154(b) by 0 days. days.

(21) Appl. No.: 14/624,056

(22) Filed: Feb. 17, 2015

(65) Prior Publication Data

US 2017/0189721 A1 Jul. 6, 2017

Related U.S. Application Data

(63) Continuation of application No. 13/619,064, filed on Sep. 14, 2012, which is a continuation of application No. 12/900,717, filed on Oct. 8, 2010, now Pat. No. 8,345,821, which is a continuation of application No. 12/077,016, filed on Mar. 14, 2008.

(60) Provisional application No. 60/918,540, filed on Mar. 16, 2007.

(51) Int. Cl.
*A61N 5/10* (2006.01)
*A61B 6/00* (2006.01)

(52) U.S. Cl.
CPC ............ *A61N 5/1067* (2013.01); *A61B 6/503* (2013.01); *A61N 5/1049* (2013.01); *A61N 5/1068* (2013.01); *A61N 2005/1061* (2013.01)

(58) Field of Classification Search
CPC ................... A61B 6/503; A61B 6/504; A61N 2005/1061; A61N 5/1049; A61N 5/1067; A61N 5/1068
See application file for complete search history.

(56) References Cited

U.S. PATENT DOCUMENTS

2005/0161051 A1* 7/2005 Pankratov ................ A61N 5/10
128/898

* cited by examiner

*Primary Examiner* — Glen Kao
(74) *Attorney, Agent, or Firm* — Wilson Sonsini Goodrich & Rosati

(57) ABSTRACT

Method and systems are disclosed for radiating a moving target inside a heart. The method includes acquiring sequential volumetric representations of an area of the heart and defining a target tissue region and/or a radiation sensitive structure region in 3D for a first of the representations. The target tissue region and/or radiation sensitive structure region are identified for another of the representations by an analysis of the area of the heart from the first representation and the other representation. Radiation beams to the target tissue region are fired in response to the identified target tissue region and/or radiation sensitive structure region from the other representation.

28 Claims, 3 Drawing Sheets

RADIATION TREATMENT PLANNING AND DELIVERY FOR MOVING TARGETS IN THE HEART

CROSS-REFERENCES TO RELATED APPLICATIONS

This application is a Continuation of U.S. Ser. No. 13/619,064 filed Sep. 14, 2012; which is a Continuation of U.S. Ser. No. 12/900,717 filed Oct. 8, 2010 (now U.S. Pat. No. 8,345,821), which application is a Continuation of U.S. Ser. No. 12/077,016 filed Mar. 14, 2008, which application claims the benefit under 35 USC 119(e) of U.S. Provisional Application No. 60/918,540 filed Mar. 16, 2007. The full disclosures, each of which are incorporated herein by reference in their entirety for all purposes.

This application is related to U.S. patent Ser. No. 11/971,399 filed Jan. 9, 2008, entitled "Depositing Radiation In Heart Muscle Under Ultrasound Guidance;" U.S. patent Ser. No. 11/971,725 filed on Jan. 9, 2008, entitled "Method for Depositing Radiation in Heart Muscle;" and U.S. Provisional Application No. 60/975,373 filed on Sep. 26, 2007, entitled "Radiosurgical Ablation of the Myocardium;" the full disclosures of which are incorporated herein by reference in their entirety.

BACKGROUND OF THE INVENTION

The present invention generally provides improved methods, devices, and systems for treatment of tissue, in many cases by directing radiation from outside the body toward an internal target tissue. Exemplary embodiments may deposit a specified radiation dose at a target in the heart muscle while limiting or minimizing the dose received by adjoining radiation sensitive structures.

In the past, targets such as tumors in the head, spine, abdomen and lungs have been successfully treated by using radiosurgery. During radiosurgery, the target is bombarded with a series of beams of ionizing radiation (for example, a series of MeV X-ray beams) fired from various different positions and orientations by a radiation delivery system. The beams can be directed through intermediate tissue toward the target tissue so as to affect the tumor biology. The beam trajectories help limit the radiation exposure to the intermediate and other collateral tissues, using the cumulative radiation dose at the target to treat the tumor. The CyberKnife™ Radiosurgical System (Accuray Inc.) and the Trilogy™ radiosurgical system (Varian Medical Systems) are two such radiation delivery systems.

Modern robotic radiosurgical systems may incorporate imaging into the treatment system so as to verify the position of the target tissue without having to rely on rigid frameworks affixing the patient to a patient support. Some systems also have an ability to treat tissues that move during respiration, and this has significantly broadened the number of patients that can benefit from radiosurgery. It has also previously been proposed to make use of radiosurgical treatments for treatment of other tissues that undergo physiological movements, including the directing of radiation toward selected areas of the heart for treatment of atrial fibrillation.

During atrial fibrillation, the atria lose their organized pumping action. In normal sinus rhythm, the atria contract, the valves open, and blood fills the ventricles (the lower chambers). The ventricles then contract to complete the organized cycle of each heart beat. Atrial fibrillation has been characterized as a storm of electrical energy that travels across the atria, causing these upper chambers of the heart to quiver or fibrillate. During atrial fibrillation, the blood is not able to empty efficiently from the atria into the ventricles with each heart beat. By directing ionizing radiation toward the heart based on lesion patterns used in open surgical atrial fibrillation therapies (such as the Maze procedure), the resulting scar tissue may prevent recirculating electrical signals and thereby diminish or eliminate the atrial fibrillation.

While the proposed radiosurgical treatments of atrial fibrillation offer benefits by significantly reducing trauma for heart patients, improvements to existing radiosurgical systems may be helpful to expand the use of such therapies. For example, movement of the tissues of the heart during a heartbeat may be significantly more rapid than movements of lung tumors induced by respiration. While well suited for treatment of lung tissues and the like, existing systems used to verify target registration may also limit radiation exposure of collateral tissues and/or avoid delays in the procedure by limiting the rate at which x-ray images are acquired during treatment. As several radiation-sensitive structures are in and/or near the heart, and as the treatment time for a single heart patient may be as long as 30 minutes or more, increasing the imaging rate and/or delaying the radiation beams when the target tissue is not sufficiently aligned may be undesirable in many cases.

In light of the above, it would be desirable to provide improved devices, systems, and methods for treating moving tissues of a patient, particularly by directing radiation from outside the patient and into target tissues of a heart. It would be particularly beneficial if these improvements were compatible with (and could be implemented by modification of) existing radiosurgical systems, ideally without significantly increasing the exposure of patients to incidental imaging radiation, without increasing the costs so much as to make these treatments unavailable to many patients, and/or without unnecessarily degrading the accuracy of the treatments and without causing collateral damage to the healthy tissue despite the movement of the target tissues during beating of the heart.

BRIEF SUMMARY OF THE INVENTION

The present invention generally provides improved medical devices, systems, and methods, particularly for radiation treatment planning and delivery for moving tissues in a heart. The invention allows improved radiosurgical treatment of tissues of the heart, often enhancing the capabilities of existing robotic radiosurgical systems for targeting tissues of the heart to mitigate arrhythmias such as atrial fibrillation or the like.

In one embodiment, a method is disclosed for radiating a moving target inside a heart comprising acquiring sequential volumetric representations of an area of the heart and defining a target tissue region and/or a radiation sensitive structure region in 3-dimensions (3D) for a first of the representations. The target tissue region and/or radiation sensitive structure region are identified for another of the representations by an analysis of the area of the heart from the first representation and the other representation. Radiation beams to the target tissue region are fired in response to the identified target tissue region and/or radiation sensitive structure region from the other representation.

In another embodiment, a method is disclosed for radiating a moving target of a wall of a heart comprising acquiring at least one volume of the heart and defining the target tissue region and/or critical structure region in 3D so that the target tissue region extends through the wall of the heart. A dose distribution is computed and radiation beams are fired to the target to obtain the simulated dose distribution transmurally through the wall of the heart.

In another embodiment, a method is disclosed for radiating a moving target inside a heart comprising acquiring a computed tomography (CT) volume and defining a transmural target tissue region. A dose distribution is computed and visualized using volume or surface rendering in 3D so as to verify transmurality.

In another embodiment, a system is disclosed for radiating a moving target inside a heart comprising a volume acquisition system for acquiring at least one CT volume of an area of the heart and a processor coupled to the image acquisition system. The processor is configured for defining the target tissue region and/or critical structure region in 3D and computing a dose distribution. A robot is coupled to the processor and a radiation beam source is supported by the robot and is coupled to the processor. The processor controls the firing of a series of the radiation beams from the radiation source so as to treat the target tissue region.

In another embodiment, a system is disclosed for radiating a moving target inside a heart comprising a volume acquisition system for acquiring a computed tomography (CT) volume and a processor coupled to the image acquisition system. the processor is configured for defining a transmural target tissue region and computing a dose distribution. A visualization system is used for visualizing the dose distribution using volume or surface rendering in 3-dimensions (3D) so as to verify transmurality.

Many different types of modeling may be used with the method and systems, including (1) volume rendering, (2) maximum intensity projection, (3) minimum intensity projection, (4) X-ray projection, (5) haptic feedback, (6). virtual fly-through, (7) stereoscopic 3D rendering, (8) virtual reality and (9) multi-planar, oblique and curved reconstruction. In some embodiments the contours of the target tissue region and/or a radiation sensitive structure region are outlined in 3D. In some embodiments an electrogram may be registered to the CT volumes. In some embodiments the moving target is a wall of a heart and the methods and systems ensure transmurality of the target.

DETAILED DESCRIPTION OF THE INVENTION

Figure 1:
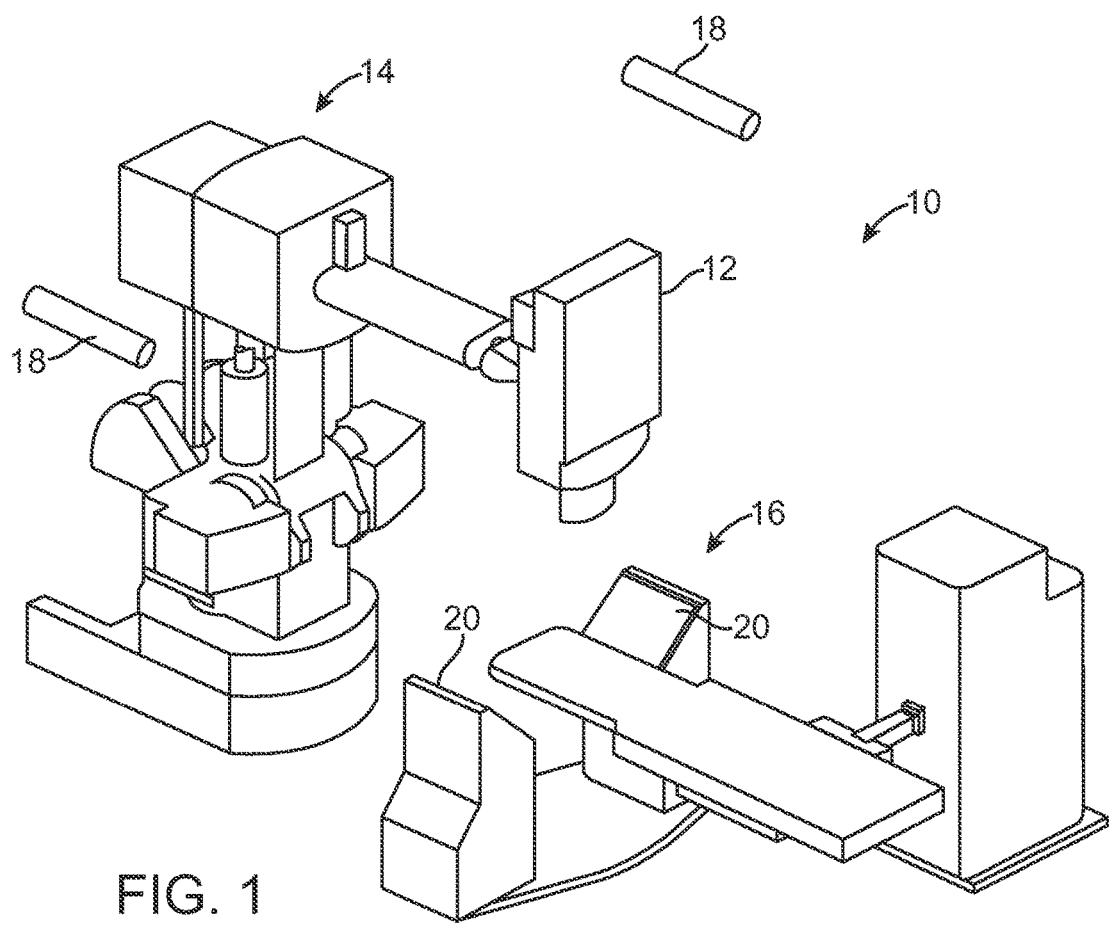
FIG. 1 is an exemplary CyberKnife stereotactic radiosurgery system for use in embodiments of the invention.

The present invention generally provides improved devices, systems, and methods for treatment of tissue, often using radiosurgical systems. The invention is particularly well suited for tracking of moving tissues such as tissues of the heart and tissue structures adjacent the heart that move with the cardiac or heartbeat cycles. Alternatively, it is also suited for tracking of moving tissues in the heart and its adjacent structures due to respiration. The invention may take advantage of structures and methods which have been developed for treating tumors, particularly those which are associated with treatments of tissue structures that move with the respiration cycle. A variety of differing embodiments may be employed, with the following description presenting exemplary embodiments that do not necessarily limit the scope of the invention.

Radiosurgery is a known method of treating targets in the body, such as tumors in the head, spine, abdomen and lungs. During radiosurgery, the target is bombarded with a series of MeV X-ray beams fired from various different positions and orientations by using a radiation delivery system, to affect the tumor biology using the cumulative radiation dose at the target. The radiation can be delivered invasively in conjunction with traditional scalpel surgery, or through a percutaneous catheter. Radiation can also be delivered non-invasively from outside the body, through overlying tissue. CyberKnife™ (Accuray Inc.) and Trilogy™ (Varian Medical Systems) are two such radiation delivery systems. Advances in stereotactic surgery have provided increased accuracy in registering the position of tissue targeted for treatment and a radiation source. For example, see U.S. Pat. Nos. 6,351,662 and 6,402,762. Stereotactic radiosurgery systems may be commercially available from ACCURAY, INC. of Sunnyvale, Calif., and BRAINLAB. The Accuray Cyberknife™ stereotactic radiosurgery system has reportedly been used to provide targeted, painless, and fast treatment of tumors.

Improvements in imaging and computer technology have led to advances in radiation treatment, often for targeting tumors of the spine and brain. The introduction of CT scanners enables surgeons and radiation oncologist to better define the location and shape of a tumor. Further improvements in imaging technology include MRI, ultrasound, fluoroscopy and PET scanners. In addition, radiation therapy has also been aided by enhancements in ancillary technologies such as simulators to help position patients and advanced computers to improve treatment planning to enable the radiation oncologist to deliver radiation from a number of different angles. Computer technology has been introduced that enable radiation oncologists to link CT scanners to radiation therapy, making treatment more precise and treatment planning faster and more accurate, thereby making more complex plans available. Such advancements allow integrated conformal therapy, in which the radiation beam conforms to an actual shape of a tumor to minimize collateral damage to the surrounding healthy tissue. By combining simulators and imaging and treatment planning computers, the irradiation can be precisely administered.

The present invention may take advantage of many components included in or derived from known radiation delivery system components. Suitable system components may comprise:

1. A linear accelerator (Linac) capable of generating the X-ray beam.
2. A mechanism to position and orient the X-ray beam.
3. A patient registration system to position and orient the target in the coordinate system of the delivery system.
4. A tracking system for tracking the target during treatment in case the target changes shape or moves between the time of, for example, a CT exam and the time of treatment, and/or during treatment.
5. A couch capable of positioning the target (patient) independent of the mechanism described in #2 above.

In exemplary CyberKnife-based systems, the above 5 items may correspond to:
1. A 6 MeV X-band X-ray Linac
2. A 6 degree-of-freedom (DOF) robotic manipulator.
3. A patient registration system consisting of:
   Two ceiling-mounted diagnostic X-ray sources
   Two amorphous silicon image detectors mounted on the floor.
4. During treatment, two orthogonal X-rays are taken and registered with the CT data by cross-correlating the X-rays with simulated X-rays generated by CT data, called digitally reconstructed radiographs (DRR).
5. The tracking system may include several light-emitting diodes (LEDs) mounted on the patent's skin to provide additional information at a rate faster than what X-rays alone may provide.
6. A couch with 5 DOF.

An exemplary Cyberknife stereotactic radiosurgery system 10 is illustrated in FIG. 1. Radiosurgery system 10 has a single source of radiation, which moves about relative to a patient. Radiosurgery system 10 includes a lightweight linear accelerator 12 mounted to a highly maneuverable robotic arm 14. An image guidance system 16 uses image registration techniques to determine the treatment site coordinates with respect to linear accelerator 12, and transmits the target coordinates to robot arm 14 which then directs a radiation beam to the treatment site. When the target moves, system 10 detects the change and corrects the beam pointing in real-time or near real-time. Real-time or near real-time image guidance may avoid any need for skeletal fixation to rigidly immobilize the target.

System 10 makes use of robot arm 14 and linear accelerator 12 under computer control. Image guidance system 16 includes diagnostic x-ray source 18 and image detectors 20, this imaging hardware comprising two fixed diagnostics fluoroscopes. These fluoroscopes provide a stationary frame of reference for locating the patient's anatomy, which, in turn, has a known relationship to the reference frame of robot arm 14 and linear accelerator 12. Image guidance system 16 can monitor patient movement and automatically adjust system 10 to maintain the radiation beam directed at the selected target tissue. Rather than make use of radiosurgery system 10 and related externally applied radiosurgical techniques to tumors of the spine and brain tissues, the invention applies system 10 to numerous cardiac conditions, and in one exemplary method to the treatment of atrial fibrillation (AF).

Tradition radiosurgery instruments without image guidance technology rely on stereotactic metal frames screwed into the patient's skull to accurately target a tumor. Traditional radiosurgery has its drawbacks, the biggest of which relate to the use of the frame, including the pain and difficulty of accurately reattaching the frame in precisely the same location, along with the inability to target tissues other than those in the neck and head. Conventional linear accelerators for these systems can also be the size and weight of an automobile. Frame-based radiosurgery is generally limited to isocentric or spherical target treatments. To allow a device which can precisely pinpoint and treat tissues throughout the body, system 10 makes use of a portable linear accelerator, such as those originally designed for industrial inspections, which can be carried on a person's back. Linear accelerators may be commercially available from SCHONBERG RESEARCH GROUP, SIEMENS, PICKER INTERNATIONAL INC. or VARIAN.

System 10 allows intensity modulated radiation therapy. Using computerized planning and delivery, intensity modulated radiation therapy conforms the radiation to the shape of (for example) a tumor. By using computers to analyze the treatment planning options, multiple beams of radiation match the shape of the tumor. To allow radiosurgery, system 10 can apply intense doses of high-energy radiation to destroy tissue in a single treatment. Radiosurgery with system 10 uses precise spatial localization and large numbers of cross-fired radiation beams. Because of the high dosage of radiation being administered, such radiosurgery is generally more precise than other radiation treatments, with targeting accuracies of 1 to 2 mm.

Linear accelerator 12 is robotically controlled and delivers pin-point radiation to target regions throughout the body of the patient. Radiation may be administered by using a portable linear accelerator such as that illustrated in FIG. 1. Larger linear accelerators may also generate the radiation in some embodiments. Such linear accelerators may be mounted on a large rotating arm that travels around the patient, delivering radiation in constant arcs. This process delivers radiation to the target tissue and also irradiates a certain amount of surrounding tissue. As a result, such radiation therapy may be administered in a series of relatively small doses given daily over a period of several weeks, a process referred to as fractionation. Each radiation dose can create some collateral damage to the healthy surrounding tissue.

In the exemplary embodiment, robot arm 14 of system 10 is part of a pure robotics system, providing six degree of freedom range of motion. In use, the surgeon basically pushes a button and the non-invasive procedure is performed automatically with the image guidance system continuously checking and re-checking the position of the target tissue and the precision with which linear accelerator 12 is firing radiation at the tumor. Image guidance system provides ultrasound guidance that gives the surgeon the position of internal organs. Image guidance system continuously checks, during a procedure, that the radiation beam is directed to the target. Alternatively the image guidance system includes an X-ray imaging system as is the case with the traditional Accuray CyberKnife™ radiosurgery system. The exemplary image guidance system takes the surgeon's hand out of the loop. The surgeon may not even be in the operating room with the patient. Instead, the image guidance system guides the procedure automatically on a real-time basis. By combining advanced image guidance and robotics, system 10 has proven effective in treating head and neck tumors without having to resort to stereotactic metal frame screwed into the skull of a patient.

The target shape may be a three-dimensional shape and may include (1) volume rendering, (2) maximum intensity projection, (3) minimum intensity projection, (4) X-ray projection, (5) haptic feedback, (6). virtual fly-through, (7) stereoscopic 3D rendering, (8) virtual reality, and (9) multiplanar, oblique and curved reconstruction.

The system 10 creates the target shape to encompass (including or surrounding) the anatomical site. The anatomical site may include an ostium of a pulmonary vein (PV), a cavotricuspid isthmus (CTI), an Atrioventricular (AV) node or junction, Sinoatrial (SA) node, His-Purkinje fibers, or ablation of areas necessary to control and treat aberrant arrhythmias, an atrial or ventricular site, neural fibers near or adjacent to the heart (ganglionic) or neural fibers in the chest or neck.

Once the target position is determined, the coordinates are relayed to robot arm 14, which adjusts the pointing of linear accelerator 12 and radiation is delivered. The speed of the imaging process allows the system to detect and adjust to changes in target position in less than one second. The linear accelerator is then moved to a new position and the process is repeated. Alternative systems may make use of laser triangulation, which refers to a method of using so-called laser tattoos to mark external points on the skin's surface so as to target the location of internal organs and critical structures. An alternative system commercialized by BRAINLAB uses a slightly different approach that measures chest wall movements.

The system is capable of directing one or more doses of radiation from outside of the patient's body toward the target shape to ablate the target shape. The quantity of absorbed in a tissue is the "dose" with the SI unit Gray (Gy=J/kg). The dose is strongly dependent on the type of radiation and the time span, also called "dwell time". An application dose rate is the dose of radiation per time (delivered or received). The dose rate delivered by a source depends on the activity of the source and the radionuclide that it contains. Biological effects of the absorbed radiation are dependent on the type of radiation and the type of tissue which is irradiated. Both total radiation dose and dose rate are important, since damage caused by radiation can be repaired between fractionated doses or during low dose rate exposure. The target dose rate may be between 15 to 80 Gy, preferably, between 25 to 40 Gy to achieve histological change at the target site without harm to other tissue. In one embodiment, the accuracy of is better than 2 mm, which is within the range of cardiac motion certain portions of the heart at or within 2 mm plus or minus.

System 10 combines robotics and advanced image-guidance to deliver true frameless radiosurgery. Multiple beams of image guided radiation are delivered by robot arm 14 mounted linear accelerator 12. The radiation can converge upon a tumor, destroying it while minimizing exposure to surrounding healthy tissue. Elimination of a stereotactic frame through the use of image guided robotics enables system 10 to treat targets located throughout the body, not just in the head. Radiosurgery is thus possible in areas such as the spine that have traditionally been difficult to treat in the past with radiosurgery, and for pediatric patients such as infants, whose skulls are too thin and fragile to undergo frame-based treatment.

System 10 allows ablation of tissue anywhere in the patient's body. The present invention uses high energy x-ray irradiation from a linear accelerator mounted on a robot arm to produce ablation of target tissue. In one example, system 10 is used to ablate tumors or other defects of the heart treatable with radiation.

Advantages of system 10 include a treatment which can be provided on an outpatient basis, providing a painless option without the risk of complications associated with open surgery. Treatment may be applied in a single-fraction or hypo-fractionated radiosurgery (usually 2 to 5 fractions) for treatment near sensitive structures. System 10 provides flexibility in approach through computer control of flexible robotic arm 14 for access to hard-to-reach locations. System 10 is capable of irradiating with millimeter accuracy. System 10 also has the ability to comprehensively treat multiple target shapes. System 10 allows isocentric (for spherical) or non-isocentric (for irregularly shaped) target shapes. The creation of the target shapes also takes into account critical surrounding structures, and through the use of robotic arm 14, harm to the critical structures surrounding may be reduced. Sophisticated software allows for complex radiation dose planning in which critical structures are identified and protected from harmful levels of radiation dose. After careful planning, the precise robotic arm can stretch to hard-to-reach areas. The precise radiation delivered from the arm then minimizes the chance of injury to critical surrounding structures, with near-real-time image-guidance system eliminating the need for rigid immobilization, allowing robot arm 12 to track the body throughout the treatment.

It may be advantageous to, for a moving target inside the heart:
1. Proscribe a dose distribution to a target region in moving tissue,
2. Simulate the dose distribution, and
3. Deliver the specified dose.

Figure 2:
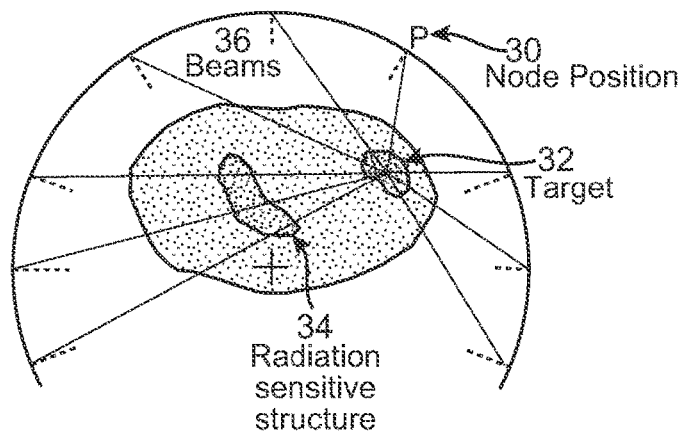
FIG. 2 schematically illustrates locations of the target, the radiation sensitive structures, the nodes and the beams in the CyberKnife system.

During treatment planning for system 10, beam nodes 30 and weights may be selected by a computer programming module to:
1. Deliver the proscribed dose to a target 32.
2. Avoid or minimize the dose delivered to radiation sensitive structures 34, such as shown in FIG. 2.

Before a treatment session, a CT volume of the target vicinity is acquired. Other imaging modalities such as MRI, PET and ultrasound may also be used. The user defines the target and any radiation sensitive structures by outlining a series of contours in slices through the CT volume. A computer program then generates the set of nodes 30 from which a set of beams 36 will be fired and the weights for each of the beams. Alternatively, the user selects the nodes and the computer program generates the weights.

If the target is inside the heart, a series of CT volumes, called a volumetric movie may be acquired to capture the motion of the target. The definition of the target and the radiation sensitive structures can be time consuming since the user may outline contours in each of the volumes in the volumetric movie. The volumetric movie may be acquired as a function of a physiologic waveform such as EKG, respiratory signal or both.

In the case where the target is inside the heart on heart muscle, radiosurgical ablation creates scar tissue and eliminates abnormally conducting tissue. Radiosurgical ablation thus has the ability to suppress arrhythmias by creating lesions at targets such as the cavotricuspid isthmus and pulmonary vein ostia. One of key objectives when defining the target on heart muscle is to ensure that the target is transmural, i.e., covers the entire thickness of the heart muscle.

The methods for defining targets in the body using CT involves the user drawing 2-dimensional contours in axial, sagittal, coronal or oblique slices generated from the CT volume. Since heart is a complex 3-dimensional shape, it is not easy to draw such contours on heart muscle in above mentioned slices to ensure that target transmurality is achieved. Embodiments of the invention eliminates this limitation by allowing target definition in 3-dimensions, and providing techniques to visualize the target on heart muscle to ensure that the target is in fact transmural.

Figure 3:
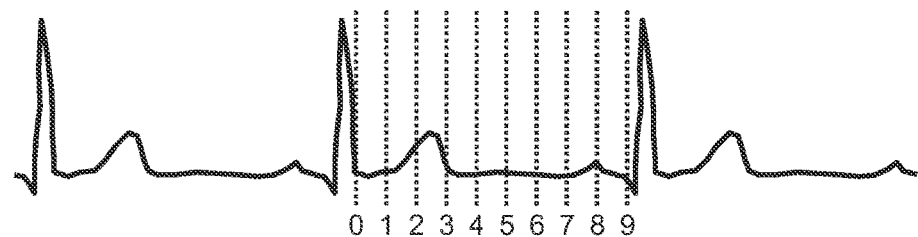
FIG. 3 graphically illustrates an EKG waveform showing the phases where CT volumes may be acquired.

Detailed Description of an Exemplary Method for Implementation in a Heart Treatment System In an exemplary new method, the user defines the target and the radiation sensitive structures much more quickly. The steps of this embodiment method may include the following:
1. Acquire a series of M CT volumes, $CT(j)$, $j=0, \ldots, M-1$, of the heart over one cardiac cycle with the patient holding his/her breath. Use a high speed CT scanner such as 64-slice Siemens SOMOTOM Definition to acquire CT volumes quickly, e.g. one volume in 83 ms. Contrast agents may be used. FIG. 3 shows a typical EKG waveform with M=10 phases where 10 CT volumes are acquired. Alternatively, the CT volumes, CT(j) could be acquired over a respiratory cycle. Additionally, the CT volumes, CT(j) may be acquired over a respiratory cycle, yet triggered to an EKG cycle.

Figure 4:
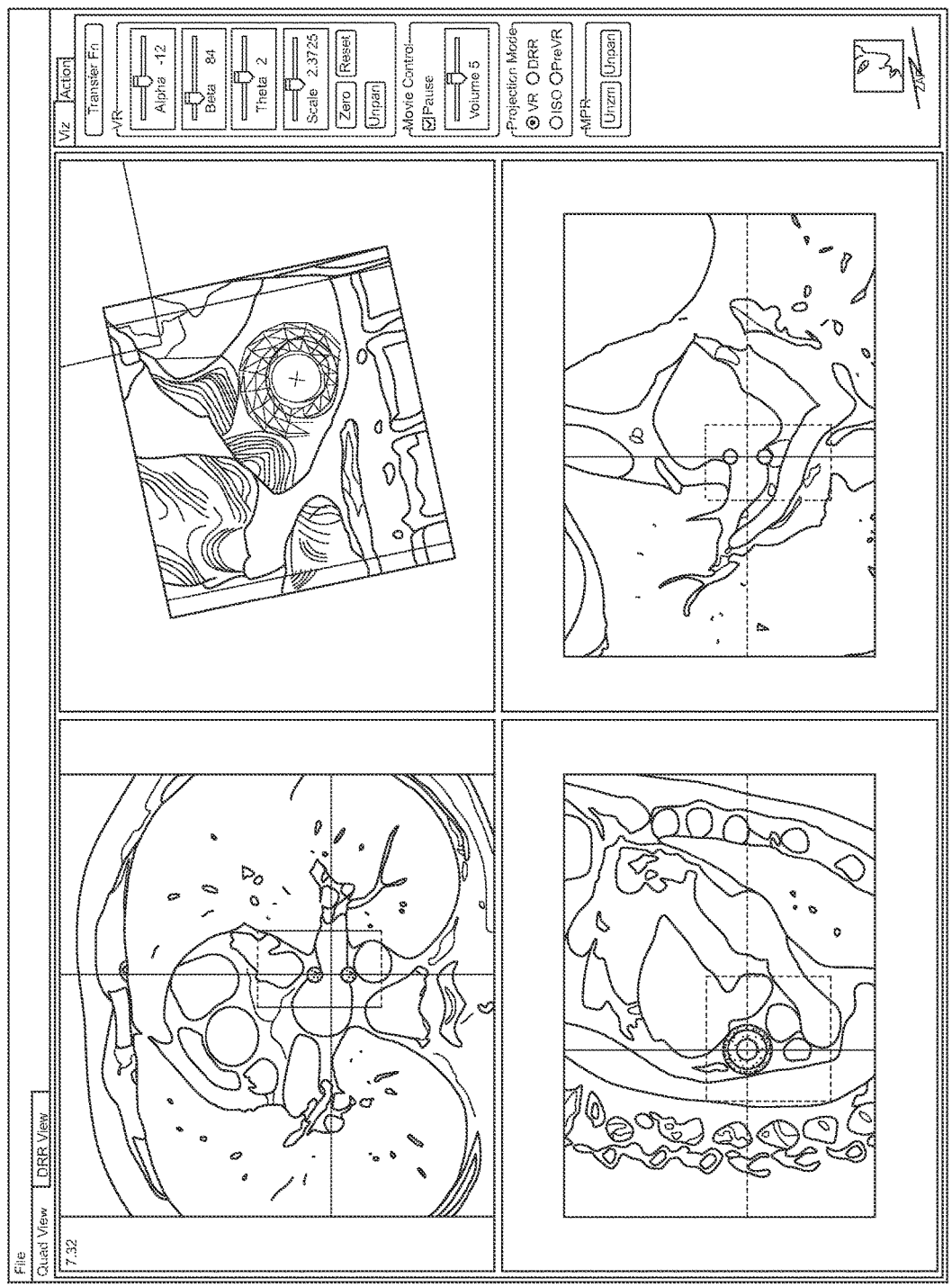
FIG. 4 illustrates a screenshot of a display showing an output obtained using an exemplary software application for loading and proscribing a target in moving tissue.

2. Load all the M CT data volumes (here in forth known as "volumetric movie") in to a data visualization computer software application module running on the processor of system 10 coupled to a suitable display device, or on a processor capable of communicating to the processor of system 10. FIG. 4 shows a screenshot of a display of an exemplary such application. Top-left, bottom-left, bottom-right views, called multi-planar reconstruction-views (or MPR views), are axial, sagittal and coronal slices through a single volume in the volumetric movie, respectively. Top right is a view, called volume rendered view (or VR view), containing a 3D representation of the volume, generated using a technique called volume rendering. The VR view also covers techniques of generating other 3D representations such as (a) maximum intensity projection, (b) minimum intensity projection and (c) X-ray projection.

3. Define the target region and radiation sensitive structures in 3D using, for example, the VR-view. The user optionally drags and drops a geometric-shape, such as a doughnut, at the target region, such as the ostia of a pulmonary vein. The application provides 3D tools to orient and place the doughnut in the correct place and orientation. The application may also provide alternative MPR-views, such as a view orthogonal to the viewing direction, oblique reconstructed views, and curved reconstructed views.

4. Additionally, surface detection techniques such as "marching cubes" can be used to detect the 3-dimensional surfaces corresponding to the borders of myocardial tissue. Using the tools provided, the user can edit these surfaces to define the target. Editing includes cutting a surfaces, clipping using a bounding box.

Figures 5A, 5B, 5C:
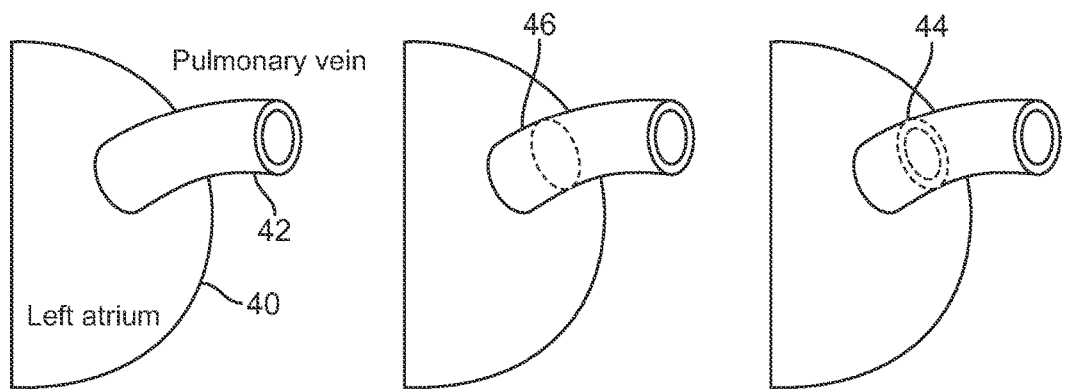
FIGS. 5(a), 5(b) and 5(c) illustrate one example of a target shape to be defined in the case of PV ostia to ensure transmurality.

FIGS. 5(a), 5(b) and 5(c) show the target shape to be defined in the case of PV ostia to ensure transmurality. FIG. 5(a) shows the anatomy including the left atrium 40 and pulmonary vein 42. FIG. 5(c) shows the target shape 44, a hollow cylinder-like shape. This ensures that the area ablated covers the full thickness of the walls of the PV ostium. The user can define this shape in 3-dimensions using the techniques described above. If they were to define this target in 2-dimensional slices, it would be very difficult.

Alternatively, the user can define a target such as the cylinder-shape 46 shown in FIG. 5(b), which encompasses the PV ostium and the blood inside it as well. This shape, called Planning Target Volume for Optimization (PTVO) can be used by the treatment planning software to generate the node-set. To quantify the dose delivered to the tissue, Planning Target Volume for Evaluation (PTVE), as shown in FIG. 5(c) can be used. In this case both PTVO and PTVE must be defined by the user to ensure transmurality. PTVO can also be automatically generated from PTVE.

If an electrogram is available, it can be registered to the CT data set and shown to the user. The user then sees the areas where the electrical activity is abnormal in the electrogram and can define the target in the electrogram it self in 3-dimensions. Since the CT is registered to the electrogram, this target can then be used to define PTVE or PTVO. Alternatively, the user can define the target in CT and visualize it in the electrogram in 3-dimensions to ensure that the target in fact covers areas where the electrical activity is high.

5. Other types of target shapes, such as spheres and polyhedrons can be used. Other types of target regions, such as, cavotricuspid isthmus or AV node can be used. Alternatively, the target and critical structure shapes can be defined using a 3D mouse or a 3D bumper tool, an improvement over the 2D mouse and 2D bumper tool found in MultiPlan™ Treatment Planning Workstation (Accuray Incorporated).

6. Optionally, the application provides the ability to view the target area from inside the heart chambers and vessels using a technique called "virtual-fly though". An airplane rudder control-like interface provides the ability for the user to visualize the myocardial walls from within the heart. The user gets the sensation that he/she is flying inside the heart chambers. Using various controls, they can bank, accelerate, decelerate, pull-up, nose-down inside the heart chambers. The user can also place the doughnut-shaped target, or any other-shaped target, at pulmonary vein ostia or any other area inside the heart.

7. Optionally, the application also provides force feedback to the user. Instead or in addition to a computer mouse, the user can use a haptic feedback device such as Omega Haptic Device (Force Dimension, Inc.). When the user grabs the target and moves it towards the target region, if the geometric shape is inside the blood, he/she will feel very little resistance to movement. If the geometric shape impinges the heart wall, he/she will feel some resistance, possibly the sensation of pushing against soft-tissue, or a rubber-like material.

8. Optionally, the application may provide a stereoscopic 3D rendering to the user. In stereoscopic 3D rendering the VR-view is generated twice using two different vantage points, typically separated by the average distance between human eyes. These left and right images are then shown to the left and right eyes of the user separately simultaneously or in rapid sequence. There are a number of display devices to view stereoscopic 3D renderings:
   a. Stereo goggles using polarizing lenses or switching displays.
   b. Stereoscopic monitors 9. The system loads the other CT volumes from the volumetric movie. It then automatically finds the location of the soft tissue region covered by the aforementioned geometric shape in all the volumes. Following this, it finds the motion of the soft tissue region throughout the cardiac cycle by using all the volumes. Correlation of a similarity function, based on CT intensities, higher order derivatives thereof, or features can be used to find the motion. One exemplary method and/or system (here employing mutual information as a similarity measure) that may be suitable for use in embodiments of the invention (without limiting other embodiments that may use other approaches) is described in an article by L. Zollei, E. Crimson, A. Norbash, W. Wells, entitled "2D-3D rigid registration of x-ray fluoroscopy and CT images using mutual information and sparsely sampled histogram estimators," CVPR 2001, which is incorporated herein by reference. Another exemplary method and/or system can be found in the deformable registration method described by J-P Thirion entitled "Image Matching as a diffusion process: an analogy with Maxwell's Demons", Medical Image Analysis (1998) Volume 2, Number 3, pp 243-260, Oxford University Press.

10A. The system then computes the dose distributions for each of the volumes in the volumetric movie. From this, it computes the average dose distribution.

10B. Alternatively, the motion of the target or critical structures that cannot be tracked can be accounted for by expanding the target and critical volumes with a margin that is based on motion estimates. The margin can be large enough to include the full amplitude of motion or it could be large enough to include the target a large percentage of the time. Expanding the target region by the full extent of the motion will result in more tissue destruction than is necessary. In radiosurgical treatment of tumors, margins have the benefit of destroying any microscopic extension of the cancer that is not visible in the images. However, in radiosurgical treatment of arrhythmias, the target structure is well known and does not include any extension, therefore, the margin should be minimized. Margins can be calculated to include the target a large percentage of the time by determining the three dimensional probability density function for the target position and then setting the margin to include some fraction of the integrated probability. The dose calculation can then be modified based on the fraction of the treatment when the target is within the volume. Multiple margins calculated with different probability levels can be used in the dose calculation. For example, if a margin is drawn around a target region to include the complete target 80% of the time, the minimum dose can be estimated as 0.8*min80, where min80 represents the minimum dose within the margin that includes the entire target 80% of the time.

In this estimate, target is considered to receive no dose during the time it spends outside of the margin. If an additional margin is drawn to include the target region 95% of the time, the minimum dose can be estimated as the lesser of (min80) and (0.8*min80+0.15*min95), where min80 is defined as above and min90 represents the minimum dose within the margin that includes the entire target 95% of the time. These calculations will underestimate the minimum dose to the target less than using a margin that includes the target 100% of the time.

Similar calculations can be made for the maximum dose to critical structures. For example, if a margin is drawn to include the complete critical structure 80% of the time, the maximum dose to any point in the critical structure can be calculated as (0.8*max80+0.2*maxField), where max80 is the maximum dose within the margin that includes the target 80% of the time and maxField represents the maximum dose in the field. If an additional margin is drawn to include the critical structure 100% of the time, the maximum dose to any point in the critical structure can be calculated as the greater of max80 and (0.8*max80+0.2*max100), where max80 is defined as above and max100 is the maximum dose within the margin that includes the critical structure 100% of the time. This will overestimate the maximum dose to the critical structure less than a margin based on including the critical structure 100% of the time.

Isotropic or anisotropic margins can be used to account for the motion. Anisotropic margins can be calculated by moving each surface point in an outward surface normal direction by a distance equal to the radius of a margin ellipsoid in the same direction as the outward surface normal. Accuracy may be improved by defining the margin ellipsoid such that its principle axes are aligned with the principle axis of the motion of the target or critical structure.

Margin estimates do not require full volumetric motion information from the target. An estimate of the target motion can be determined by the position measurements for one point on the target at multiple times during the cardiac cycle. This can be obtained from simultaneous biplanar fluoroscopic images showing the tip of a catheter that has been placed in the heart touching the cardiac structure of interest. Alternatively, real-time 3D ultrasound could be used to determine the motion of structures of interest non-invasively.

11. The robot then fires the beams from predetermined locations to create the simulated dose distribution.

12. Alternatively, the user may visualize the 3D or 4D dose distributions using a volume rendering of the dose distribution. Optionally, 3D fly though and haptic feedback can be used to visualize and interact with the 3D or 4D dose distributions.

Figure 6:
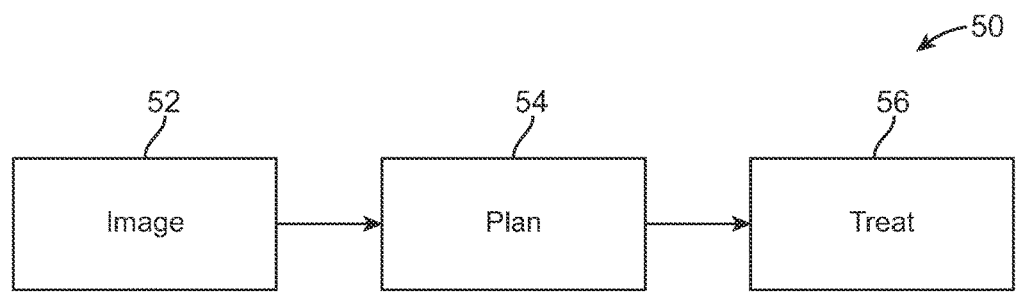
FIG. 6 schematically illustrates a method for treating a target tissue using a radiosurgical system.

Referring now to FIG. 6, a relatively simple treatment flowchart 50 can represent imaging 52, planning 54, and treatment 56 steps and/or structures used before and during radiosurgical treatment according to embodiments of the present invention. Imaging 52, planning 54, and treatment 56 structures may include an associated processor module. The processor modules will typically comprise computer processing hardware and/or software, with the software typically being in the form of tangible media embodying computer-readable instructions or code for implementing one, some, or all of the method steps described herein. Suitable tangible media may comprise a random access memory (RAM), a read-only memory (ROM), a volatile memory, a non-volatile memory, a flash memory, a magnetic recording media (such as a hard disk, a floppy disk, or the like), an optical recording media (such as a compact disk (CD), a digital video disk (DVD), a read-only compact disk, a read/write compact disk, a memory stick, or the like). The various modules described herein may be implemented in a single processor board of a single general purpose computer, or may be run on several different processor boards of multiple proprietary computers, with the code, data, and signals being transmitted between the processor boards using a bus, a network (such as an Ethernet, intranet, or internet), via tangible recording media, using wireless telemetry, or the like. The code may be written as a monolithic software program, but will typically comprise a variety of separate subroutines and/or programs handling differing functions in any of a wide variety of software architectures, data processing arrangements, and the like. Nonetheless, breaking the functionality of the program into separate modules is useful for understanding the capabilities of the various aspects of the invention.

Addressing the imaging block 52 of block diagram 50 in FIG. 6, a time-sequence of 3-D volumes may be acquired using computed tomography (CT), magnetic resonance imaging (MRI), ultrasound imaging, X-ray imaging, optical coherence tomography, a combination of these or other imaging modalities, and/or the like. In some embodiments, corresponding EKG signals may also be received by the image processor module, and the processor may optionally use the EKG signals to time the acquisition of the 3-D volumes. In other embodiments, the respiratory signal may also be received by the image processor module, and the processor may optionally use the respiratory signal to time the acquisition of the 3D volumes.

CT volumes may be acquired using a variety of different approaches. A cardiac gated CT volume may be acquired at a particular phase of the EKG cycle. Two variations of cardiac gated CT may include a held-breath version and a free-breathing version. In the held-breath cardiac gated CT, the patient is holding their breath (typically either at full inspiration or full expiration), so that respiration motion is absent while the data is acquired. In the free breathing cardiac gated CT, the patient is breathing freely. The CT volume may be acquired at a desired point of the respiration cycle. By measuring the respiration wave form, the exact respiratory phase at which the CT volume is acquired can be known (similar to the known cardiac phase at which the CT volume is acquired). In either variation, both the cardiac phase and the respiration cycle phase can be identified for the cardiac gated CT.

A cardiac gated 4-dimensional CT can be generated by acquiring a time series of cardiac gated CT volumes at a series of desired EKG phases. Once again, the 4-D cardiac gated CT can be a held-breath type or a free-breathing type (as described above). Additionally, regarding the free-breathing cardiac gated 4D CT, the resulting series of CT volumes may be acquired at the same EKG phase, typically throughout the respiration cycle. By associating each CT volume with the associated phase of the respiration cycle, the time series CT volumes can be used to model respiratory-induced motion of tissue while minimizing the cardiac motion artifacts.

Yet another type of volume which may be acquired is the respiratory-gated CT volume. Such CT volumes may be acquired at a particular phase of the respiration cycle. Respiratory gating of CT may be performed prospectively or retrospectively. The cardiac motion may generally be ignored in this type of CT volume, so that the rapidly moving cardiac structures may be blurry in such CT volumes. In a related respiratory-gated 4-D CT volume, a series of respiratory-gated CT volumes are acquired at a series of respiratory phases.

Note that the tissue structure which will be targeted need not necessarily be visible in the image, so long as sufficiently contrasting surrogate imagable structures are visible in the images to identify the target tissue location. The imaging used in many embodiments will include a time sequence of three dimensional tissue volumes, with the time sequence typically spanning one or more cycles (such as a cardiac or heartbeat cycle, a respiration or breathing cycle, and/or the like).

The series of radiation beams are planned, typically by a surgeon using a user interface (such as a display and keyboard, mouse, or other input device) to communicate with a plan processor module. Based on the images, a plan 54 will be prepared for treatment of the target tissue, with the plan typically comprising a series of radiation beam trajectories which intersect within the target tissue. The processor module may make use of the model (including the tissue movements) to determine dosages in the target, collateral, and critical or sensitive tissues. The radiation dose within the target tissue should be at least sufficient to provide the desired effect (often comprising ablation of tissue, inhibition of contractile pathways within the heart, inhibition of arrhythmogenesis, and/or the like). Radiation dosages outside the target tissues will decrease with a relatively steep gradient so as to inhibit damage to collateral tissues, with radiation dosages in specified sensitive and/or critical tissue structures often being below a desired maximum threshold to avoid deleterious side effects. Embodiments of the invention may employ the 3-D volumes acquired in the imaging step 52 during the planning 54, with exemplary embodiments making use of the motion model represented by the time sequence of 3-D tissue volumes so as to more accurately identify exposure of radiation outside of the target, within sensitive tissue structures, inside the target, and the like. Planned timing of some or all of a series of radiation beams may be established based on the cardiac cycle, the respiration cycle, and/or the like so as to generate the desired dosages within the target tissue, so as to minimize or inhibit radiation exposure to critical structures, and/or to provide desired gradients between the target tissue and collateral or sensitive structures. In some embodiments, the order of the planned radiation beams may be altered and/or the trajectories of the radiation beams may be calculated in response to the motion of the model volume.

Once the plan 54 is established, the treatment 56 can be implemented. The treatment will often make use of a processor to direct movement of a robotic structure supporting a radiation beam source, along with registration, validation, and/or tracking modules which enhance accuracy of the treatment. Tracking may employ the motion model developed during imaging 52, and/or may also employ a separate intra-operative motion model. Alternatively, no motion model will be used, instead the target location computed from real-time image data will be used for tracking. The treatment 56 step and the associated hardware may use a sensor and/or input for physiological wave forms such as the respiration phase, cardiac phase, and the like for use in such tracking.

In one embodiment, an EKG sensor may be coupled to the patient to provide EKG signals to a targeting processor module. The targeting module configures the robot so as to position and orient the linear accelerator (or other radiation source) toward the target tissue along the desired trajectory for a particular radiation beam from among the series. Once the moving target tissue and the beam trajectory are appropriately aligned, the tracking module may fire the radiation beam by energizing the linear accelerator. Hence, the tracking module benefits from the motion model developed during the imaging steps, and the model may optionally be revised using data obtained immediately before and/or during treatment.

Advantageously, the treatments described herein can be iterative. Rather than target many foci or regions as is often done in an invasive procedure, externally applied radiosurgical ablation can address one or more target shapes on one day, and the then other target shapes on another day as needed. The interim period between treatments can be used to access the need for subsequent treatments. Such iterative or fractionated treatment is thus more conservative than current methods.

Suitable types of radiation, including particle beam radiation, may be employed. For example, the present invention encompasses the use of a GammaKnife™ radiosurgery system to ablate the moving tissue. Although gamma radiation could be administered during open heart or other invasive procedures, the currently preferred applications are substantially non-surgical.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method of radiating a moving target with a desired radiation dose, the target comprising a target tissue having blood flowing therethrough, the target tissue having a tissue surface including an inner surface bordering the blood and an outer surface, the method comprising:
   acquiring a series of computed tomography (CT) volumes encompassing the target tissue;
   identifying the target in three dimensions in the acquired CT volumes by visualizing a three dimensional surface rendering of the tissue surface of the target tissue and inputting the target with reference to the three dimensional surface rendering;
   computing a treatment plan according to the identified target;
   computing a dose distribution according to the computed treatment plan;
   visualizing a three dimensional display of the dose distribution superimposed with the three dimensional surface rendering of the tissue surface of the target tissue so as to verify the desired radiation dose at the target; and
   delivering the dose distribution to the target tissue to treat the target.

2. The method of claim 1, wherein the step of visualizing the display of the dose distribution comprises at least one of: 1) volume rendering, 2) maximum intensity projection, 3) minimum intensity projection, 4) X-ray projection, 5) haptic feedback, 6) virtual fly-through, 7) stereoscopic 3D rendering, 8) virtual reality, and 9) multi-planar, oblique and curved reconstructions.

3. The method of claim 1, wherein the treatment plan comprises a plurality of radiation beam trajectories which intersect within the target.

4. The method of claim 1, wherein the target comprises a tumor.

5. The method of claim 1, wherein the target comprises heart muscle and wherein the identified target is transmural.

6. The method of claim 1, further comprising defining a radiation sensitive structure relative to the acquired CT volumes by visualizing the three dimensional surface rendering of the tissue surface of the target tissue and identifying the radiation sensitive structure with respect to the three dimensional surface rendering.

7. The method of claim 6, further comprising adjusting the computed treatment plan based on the defined radiation sensitive structure.

8. The method of claim 1, further comprising registering a three dimensional electrogram with the acquired CT volumes.

9. The method of claim 1, further comprising acquiring a pair of images of the target during treatment and registering the CT volumes with the pair of images to check a position of the target during treatment.

10. The method of claim 1, wherein the identified target is non-isocentric.

11. The method of claim 1, further comprising expanding the identified target with a margin that is based on motion estimates.

12. The method of claim 11, wherein the margin includes the identified target during at least 80% of a target motion time.

13. The method of claim 1, wherein the series of CT volumes comprises a time series of CT volumes distributed throughout a movement cycle of the moving target; wherein a dose distribution is calculated for each of the acquired CT volumes; and wherein the step of visualizing a three dimensional display of the dose distribution comprises visualizing a four dimensional display of the dose distribution.

14. A non-transitory computer-readable storage medium comprising a set of computer executable instructions for treating a moving target, the target comprising a target tissue having blood flowing therethrough, the target tissue having a tissue surface including an inner surface bordering the blood and an outer surface, wherein execution of the instructions by a computer processor causes the processor to carry out the steps of:
   receiving a series of computed tomography (CT) volumes encompassing the target tissue;
   displaying on a display device a three dimensional surface rendering of the target tissue;
   receiving user input identifying the target in three dimensions with reference to the three dimensional surface rendering of the target tissue;
   computing a treatment plan according to the user identified target;
   computing a dose distribution according to the computed treatment plan;
   displaying on the display device a three dimensional visualization of the dose distribution superimposed with the three dimensional surface rendering of the tissue surface of the target tissue; and
   delivering the dose distribution to the target tissue to treat the target.

15. The non-transitory computer-readable storage medium of claim 14, wherein the processor carries out the step of displaying the dose distribution by utilizing at least one of: 1) volume rendering, 2) maximum intensity projection, 3) minimum intensity projection, 4) X-ray projection, 5) haptic feedback, 6) virtual fly-through, 7) stereoscopic 3D rendering, 8) virtual reality, and 9) multi-planar, oblique and curved reconstructions.

16. The non-transitory computer-readable storage medium of claim 14, wherein the treatment plan comprises a plurality of radiation beam trajectories which intersect within the target.

17. The non-transitory computer-readable storage medium of claim 14, wherein the processor further carries out a step of receiving user input defining a radiation sensitive structure with respect to the three dimensional surface rendering of the target tissue.

18. The non-transitory computer-readable storage medium of claim 17, wherein the processor further carries out a step of adjusting the computed treatment plan based on the user defined radiation sensitive structure.

19. The non-transitory computer-readable storage medium of claim 14, wherein the processor further carries out a step of registering a three dimensional electrogram with the received CT volumes.

20. The non-transitory computer-readable storage medium of claim 14, wherein the processor further carries out a step of receiving a pair of images of the target during treatment and a step of registering the CT volumes with the pair of images to check a position of the target during treatment.

21. The non-transitory computer-readable storage medium of claim 14, wherein the processor further carries out a step of expanding the identified target with a margin that is based on motion estimates.

22. The non-transitory computer-readable storage medium of claim 14, wherein the series of CT volumes comprises a time series of CT volumes distributed throughout a movement cycle of the moving target; wherein a dose distribution is calculated for each of the received CT volumes; and wherein the step of displaying the dose distribution comprises displaying on the display device a four dimensional display of the dose distribution.

23. A system for radiating a moving target inside a target tissue or on a blood vessel, the system comprising:
   an image receiving apparatus for receiving CT volumes encompassing the target;
   a user input device for receiving user input defining a radiation target region with reference to a three dimensional surface rendering of the target tissue;
   a processor coupled with the image receiving apparatus and the user input device, the processor configured to:
      i) compute a treatment plan according to the received user input defining the radiation target region,
      ii) compute a dose distribution according to the computed treatment plan;
      iii) generate the three dimensional surface rendering of the target tissue using the received CT volumes;
      iv) generate a three dimensional surface rendering of the dose distribution;
   a display coupled with the processor for displaying the three dimensional surface rendering of the target tissue and the three dimensional surface rendering of the dose distribution; and
   a radiation delivery device coupled with the processor, the radiation delivery device configured to deliver radiation to the target region according to the computed dose distribution.

24. The system of claim 23, wherein the user input device is further configured to receive user input defining a radiation sensitive structure relative to the three dimensional surface rendering of the target tissue.

25. The system of claim 24, wherein the processor is further configured to adjust the computed treatment plan based on the user defined radiation sensitive structure.

26. The system of claim 23, wherein the processor is further configured to register a three dimensional electrogram with the received CT volumes.

27. The system of claim 23, further comprising an image guidance system, the image guidance system configured to acquire a pair of images of the target during treatment and to register the CT volumes with the pair of images to check a position of the target during treatment.

28. The system of claim 23, wherein the image receiving apparatus is configured to receive a time series of CT volumes distributed throughout a movement cycle of the moving target; wherein the processor is further configured to calculate a dose distribution for each of the received CT volumes; and wherein the display is configured to display a four dimensional surface rendering of the dose distribution.

* * * * *